United States Patent
Mkrtchyan

(10) Patent No.: US 10,478,514 B2
(45) Date of Patent: Nov. 19, 2019

(54) METHODS FOR INACTIVATING, ON MEDICAL INSTRUMENTS AND DEVICES, VIRUSES CONTAINING RNA AND DNA, AND APPARATUSES FOR IMPLEMENTATING SAME

(71) Applicant: Ovik Leonardovich Mkrtchyan, Tashkent (UZ)

(72) Inventor: Ovik Leonardovich Mkrtchyan, Tashkent (UZ)

( * ) Notice: Subject to any disclaimer, the term of this patent is extended or adjusted under 35 U.S.C. 154(b) by 226 days.

(21) Appl. No.: 15/119,791

(22) PCT Filed: May 13, 2015

(86) PCT No.: PCT/UZ2015/000001
§ 371 (c)(1),
(2) Date: Aug. 18, 2016

(87) PCT Pub. No.: WO2015/179880
PCT Pub. Date: Nov. 26, 2015

(65) Prior Publication Data
US 2017/0056538 A1    Mar. 2, 2017

(30) Foreign Application Priority Data
May 23, 2014    (UZ) .................................... 20140210

(51) Int. Cl.
*A61L 2/00* (2006.01)
*C12N 13/00* (2006.01)
*A01N 43/16* (2006.01)
*G01N 21/00* (2006.01)
*A61L 2/08* (2006.01)
(Continued)

(52) U.S. Cl.
CPC .............. *A61L 2/084* (2013.01); *A61L 2/0052* (2013.01); *A61L 2/088* (2013.01); *A61L 2/18* (2013.01); *C12N 7/00* (2013.01); *C12N 7/04* (2013.01); *A61L 2202/17* (2013.01); *A61L 2202/24* (2013.01); *C12N 2730/10161* (2013.01)

(58) Field of Classification Search
CPC ........... A61L 27/18; C12N 15/00; A01N 1/02; A01N 43/16
USPC ...................... 422/22–24; 250/455.11, 492.1; 435/173.3, 2; 514/457
See application file for complete search history.

(56) References Cited

U.S. PATENT DOCUMENTS

| | | | | |
|---|---|---|---|---|
| 2008/0206843 | A1* | 8/2008 | Croud | A01N 37/16 435/264 |
| 2014/0127077 | A1* | 5/2014 | Rock | A61L 2/0088 422/28 |

FOREIGN PATENT DOCUMENTS

WO    WO 2015 179880    5/2015

OTHER PUBLICATIONS

Search Report in corresponding PCT/UZ2016/000001.

* cited by examiner

*Primary Examiner* — Monzer R Chorbaji
(74) *Attorney, Agent, or Firm* — Van Dyke Law; Raymond Van Dyke

(57) ABSTRACT

Methods and apparatuses for inactivating RNA and DNA within viruses situated on medical instruments. Through the use of photochemicals and photoactivation by monochromatic light, medical instruments can be rendered safer. A solution of methylene blue having a concentration of 0.01-0.02% by means of interaction with light in the emission spectrum of monochromatic emitters having wavelengths
(Continued)

ranging between 582 and 592 nm or between 658 and 662 nm and an overall light output of at least 280 lumens (lm), wherein the instruments are kept in said solution for about 90 minutes.

7 Claims, 4 Drawing Sheets

(51) Int. Cl.
*C12N 7/04* (2006.01)
*C12N 7/00* (2006.01)
*A61L 2/18* (2006.01)

METHODS FOR INACTIVATING, ON MEDICAL INSTRUMENTS AND DEVICES, VIRUSES CONTAINING RNA AND DNA, AND APPARATUSES FOR IMPLEMENTATING SAME

CROSS REFERENCE TO RELATED PATENT APPLICATIONS

The present invention is a United States nationalization of PCT/UZ2015/000001, filed May 13, 2015, entitled "METHOD OF RNA AND DNA VIRUSES INACTIVATION ON MEDICAL INSTRUMENTS AND A DEVICE FOR ITS IMPLEMENTATION," and claims priority from Uzbekistanian Patent Application No. IAP 2014 0210, filed May 23, 2014, of the same name, the subject matters of which are incorporated by reference herein in their entirety.

TECHNICAL FIELD

The invention is generally related to photodynamic inactivation of RNA and DNA viruses on medical instruments.

BACKGROUND OF THE INVENTION

During the last years of the 20th Century and at the beginning of the 21$^{st}$ Century, there have been a number of virus-related deaths across the world, with a high risk of threat for humankind's survival. Also, a growing number of people are being infected, especially with hepatitis B (hereinafter—HBV), and hepatitis C (hereinafter HCV), mostly infected by virus-laden medical instruments (surgical, dental, ophthalmic, gynecologic and others), which cannot be sterilized enough under high temperature or by autoclaving. Also, HBV and HCV are resistant to many disinfectants used in medicine. Thus, the complete removal of viral particles from the surface of medical instruments and mechanical methods are not feasible. Consequently, virus particles capable of replication and infecting people are stored on the medical tools themselves. For human infection and disease development, the existence of even one particle of HBV or HCV in blood is enough. This leads to a high risk of contracting viral infections of patients with medical procedures. Consequently, there is an urgent need to develop a more effective method for the inactivation (deprivation of the ability to replicate) of RNA and DNA viruses and particles on medical instruments.

It is clear that photodynamic inactivation of DNA and RNA viruses is based on the ability of some chemical substances (photosensitizers), when exposed to light, change to a photoactive condition and generate active forms of oxygen. The abovementioned forms of oxygen are highly toxic compounds, which make for photodynamic activities that are employed in practicing the present invention.

There is a known method of inactivating viruses in biological fluids by processing a biological fluid with light for the inactivation of contaminants, such as viruses. According to this method light intensity of at least 30 mW/cm$^2$ which affect the biological fluid is created. Biological fluid includes a certain amount of the photochemical agent (photosensitizer). When the interaction of the photochemical agent with a light-activated, photochemical agent takes place, it provides viral inactivation.

A famous method is based on the activation of methylene blue in its interaction with light having an intensity of at least 30 mW/cm$^2$. Methylene blue may be disposed within a biological fluid, and may interact with the light for a period between approximately 0.3 and 30 minutes. According to the invention, the use of known high intensity light with a biological fluid, such as blood or blood plasma containing a predetermined amount of methylene blue, enhances the effect of methylene blue in killing viruses. Methylene blue is activated by high intensity light having wavelengths from about 550 nm to 700 nm, with a peak at 663 nm. The light absorption in this range provides the activation of methylene blue. Also, the prior art shows techniques for creating high-intensity light using high pressure sodium lamps.

However, the use of these known methods for inactivating RNA and DNA containing viruses on instruments is not effective because of the high-energy intensity, the structural complexity and laboriousness of the required operation necessary.

Also, existing techniques for the inactivation of RNA and DNA viruses for medical instruments are also shown in certain medical fields and their instruments, e.g., dental, gynecological, surgery, ophthalmic, and such, where, after use, the instruments are subjected to preliminary mechanical treatment and water washing with detergents (soap solution, washing powder). Here, after thorough rinsing with tap water, the instruments are immersed in a cuvette instrument filled with a solution of methylene blue. The Cuvette with the tools are so immersed in the camera setup on a rotating pan. Unit door tightly closed, the timer is set exposure time include monochromatic light emitter is mounted above the cuvette, and the motor rotation pan. The process of inactivation of viruses on the surface of medical instruments in this fashion continued for 45 minutes, while processing with monochromatic light of wavelength 590 nm.

However, the usage of these known methods of DNA and RNA virus inactivation techniques on medical instruments are not also effective due to the increased energy intensity and structural complexity. In addition, given that the methylene blue (a photochemical agent) is capable of providing maximum activation only in the interaction with monochromatic light of wavelength 590 nm, current methodologies neither disclose nor suggest the particular methodologies and apparatuses, as set forth in the instant Specification.

SUMMARY OF THE INVENTION

A primary goal of the present invention is to develop an efficient, with minimal labor and energy consumption method for inactivating RNA and DNA viruses on medical instruments, by achieving maximum activation of the photochemical agent in the interaction with monochromatic light.

This aim is achieved by a preferred method of inactivation of RNA and DNA viruses on medical instruments, according to the principles of the present invention, includes a preliminary mechanical cleaning and washing of the infected tools, their subsequent exposure in an aqueous solution of methylene blue, with a maximum activation of the interaction of monochromatic light with a solution, preferably in an aqueous 0.01-0.02% solution of methylene blue concentration, providing maximal activation. Further, the inactivation is effected by interaction with light in the spectrum of monochromatic radiation emitters with wavelength range of 658-662 nm and 582-592 nm or tools kept in the solution for 90 minutes.

A feature of the claimed process is that the methylene blue solution is radiated by monochromatic light flux with wavelength 590 nm or 660 nm, which corresponds to the wavelength of the absorption spectrum of methylene blue. For this purpose, a special source of radiation in the emission spectrum monochromatic emitters with a wavelength range of 582-592 nm, and, accordingly the maximum specific content of a monochromatic beam at 590 nm wavelength and the emission spectrum monochromatic emitters with a wavelength range 658-662 nm and the specific content of monochromatic beam with maximum wavelength of 660 nm.

The appropriateness of the aforementioned methylene blue wavelength and the wavelength of monochromatic light flux is the photoactivation of methylene blue. When sufficient photoactivation quantum energy molecules of methylene blue are absorbed, the electrons excite in their atoms. As a result, the molecules themselves become sources of scattered light of the same wavelength (classical scattering).

Under the influence of light quanta, emitted by the photoactivated molecules of methylene blue, there is photoactivation of molecules, which are in the "shadow" relating to monochromatic radiator installation. Thus, to so treat with photoactivation of methylene blue molecule, as in the path of light rays emitter, all molecules in direct contact, and all that are in the "shadow" relative to it, realizes the full effect of the treatment, i.e., the sterilization necessary. Inactivation of RNA and DNA viruses for medical instruments can be carried out in a room-temperature photoactivated liquid, e.g., a 0.01-0.02% solution of methylene blue (Methylene Blue).

In one example, the aforementioned 0.01-0.02% methylene blue solution was subjected to a monochromatic light flux wavelength 590 nm or 660 nm, which corresponds to the wavelength of the absorption spectrum of methylene blue. Preferably, a monochromatic light beam wavelength from 660 nm to 590 nm or a monochromatic emitter is created. Total energy consumption of devices implementing the light treatment is preferably about 50 W, and the light output must be at least 280 lumens (lm). Under the influence of monochromatic light flux wavelength of 590 nm or 660 nm (corresponding to the wavelength of the absorption spectrum of methylene blue) the photoactivation of methylene blue molecules occurs. Photoactivated molecules of methylene blue actively enter into a strong bond with a pair of nucleic acids, e.g., guanine and cytosine, and locks them in the chain of RNA or DNA viruses. Viruses with such inactivated RNA and DNA, when later entering a person's blood, are thus not capable of destroying cells and replicating inside host cells. It means that they completely lose their virulence and pathogenic properties (ability to infect and cause disease). Moreover, the photoactivated molecules of methylene blue promote the formation of reactive atomic oxygen, which strengthens the denaturation process of nucleic acids of RNA and DNA viruses.

Methods for the aforementioned inactivation are shown in the various embodiments set forth in more detail hereinbelow.

BRIEF DESCRIPTION OF DRAWINGS

While this Specification concludes with claims particularly pointing out embodiments and distinctly claiming the subject matter that is regarded as forming the present invention, it is believed that the invention will be better understood from the following Description taken in conjunction with the accompanying Drawings, where like reference numerals designate like system signal flow and other mechanical elements, in which:

DETAILED DESCRIPTION OF THE INVENTION

Figure 1:
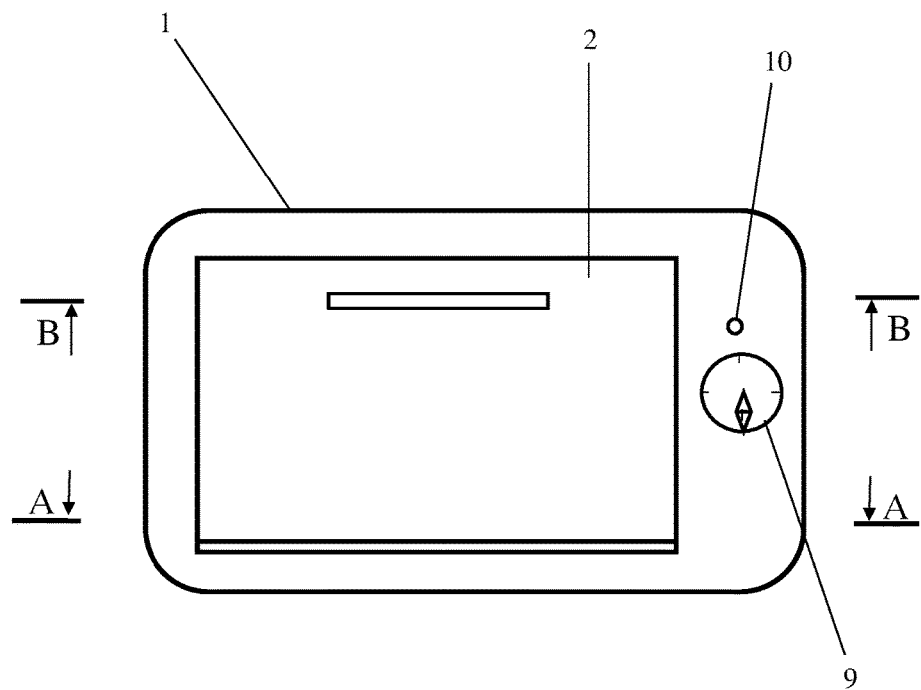
FIG. 1 illustrates an exemplary apparatus for the inactivation of RNA and DNA of viruses on medical and other instruments placed therein and treated pursuant to the principles set forth in the present Specification.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

Medical instruments, such as dental, gynecological, surgical, ophthalmic and others, after being used in patients, are subjected to preliminary mechanical cleaning and washing in water with detergents (soapy water, detergents). Thereafter, these instruments are rinsed thoroughly in tap water and then immersed into a round cuvette device in 0.01-0.02% solution of methylene blue. The instruments or tools are put on the bottom of the cell stack in a single layer so that they are completely covered with the aforementioned solution of methylene blue. Then, the cell stack with the tools are mounted on the base of the camera unit. With the unit door tightly closed, the timer is set to the selected exposure time toggle switch. At the same time the door is securely closed and till deactivation the timer should not be opened. When the device of the camera automatically turns on the panel radiator monochromatic light mounted above the cuvette. The process of inactivation of viruses present on the surface of medical instruments.

After switching off the timer, the device board's door is opened, and the cell stack with the tools is extracted. The tools are removed from the solution with tweezers and the methylene blue is rinsed off thoroughly in distilled water. Thereafter, the conventional tools may be further sterilized.

The photoactivatable fluid to inactivate DNA or RNA viruses is preferably a 0.01-0.02% solution of methylene blue (Methylene Blue) in distilled water. A 0.01-0.02% solution photoactivated liquid is preferably prepared by dissolving Methylene Blue, respectively 1.0-2.0 g, in 10 liters of distilled water in a clean container.

The aforementioned 0.01-0.02% methylene blue solution is preferably preserved in a clean container for about 10 days. A portion of the 0.01-0.02% solution of methylene blue is suitable for 3-fold use within 1 day. Visually, the loss of transparency (turbidity) or plaque formation on the surface of a solution of methylene blue is considered unsuitable for virus inactivation. In this case, the solution is prepared anew.

The known prior art in this area, at best involves devices having a flat-bottomed cell fluid and located above the radiation source, with a means for rotating the cell, means for fluid turbulence, and a battery of radiators of monochromatic visible light to inactivate liquid having photoactive properties. The process of inactivation of viruses present on the surface of medical instruments continues for 45 minutes while processing monochromatic light of wavelength 590 nm.

However, the use of these known systems for the inactivation of RNA and DNA viruses on medical instruments is not effective due to the increased energy intensity required and the structural complexity of the configuration needed. In addition, methylene blue (photochemical agent), although capable of providing maximum activation of the interaction with monochromatic light of wavelength 590 nm, the devices of the prior art do not disclose the conditions and circumstances involving the required lighting.

A basis of the present invention, however, is to develop a simplified design, with minimal labor and energy expenditures for the inactivation of RNA and DNA viruses on medical instruments, by achieving maximum activation of the photochemical agent in the interaction with monochromatic light, thereby distinguishing the instant technique and devices from the less efficient prior art.

The problem is solved by the fact that the setting for the inactivation of RNA and DNA viruses on medical instruments, includes a hermetically-sealed housing with a camera, housed in a chamber container to hold the tools, which is filled with a solution of methylene blue, and installed with an emitter of monochromatic light source, where, according to the present invention, a monochromatic light source is arranged in the emission spectrum monochromatic emitters with a wavelength range of 582-592 nm and 658-662 nm, with a total capacity of not less luminous flux 280 lm. As a monochromatic emitter, Light emitting diodes (LEDs) were selected in a preferred embodiment.

Figure 2:
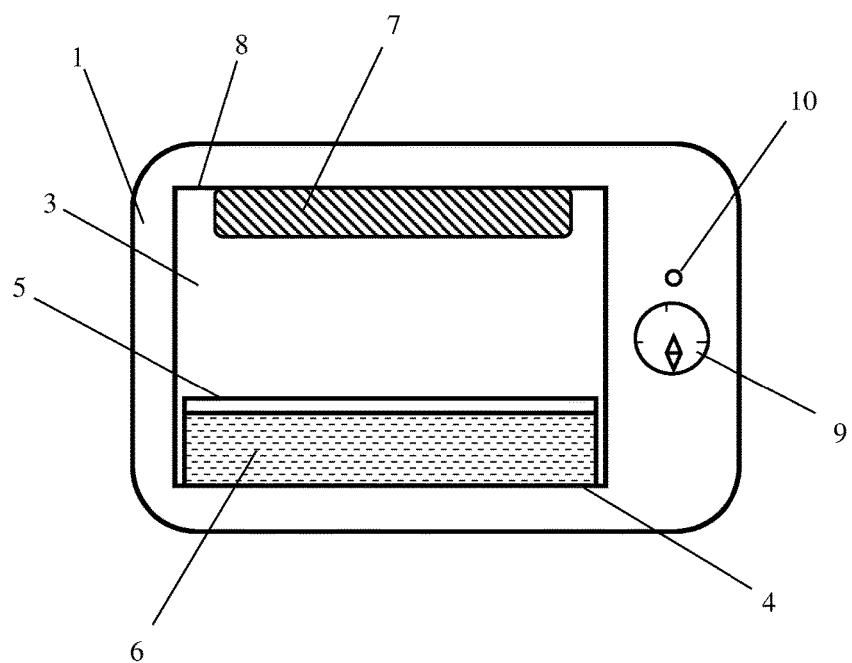
FIG. 2 illustrates another exemplary embodiment of the present invention, showing various interior components that may be employed in practicing the teachings of the present invention, and which may be visible upon opening a door of an apparatus, such as shown in FIG. 1, and allowing interaction with the interior and the sealing thereof for treatment.
Figure 3:
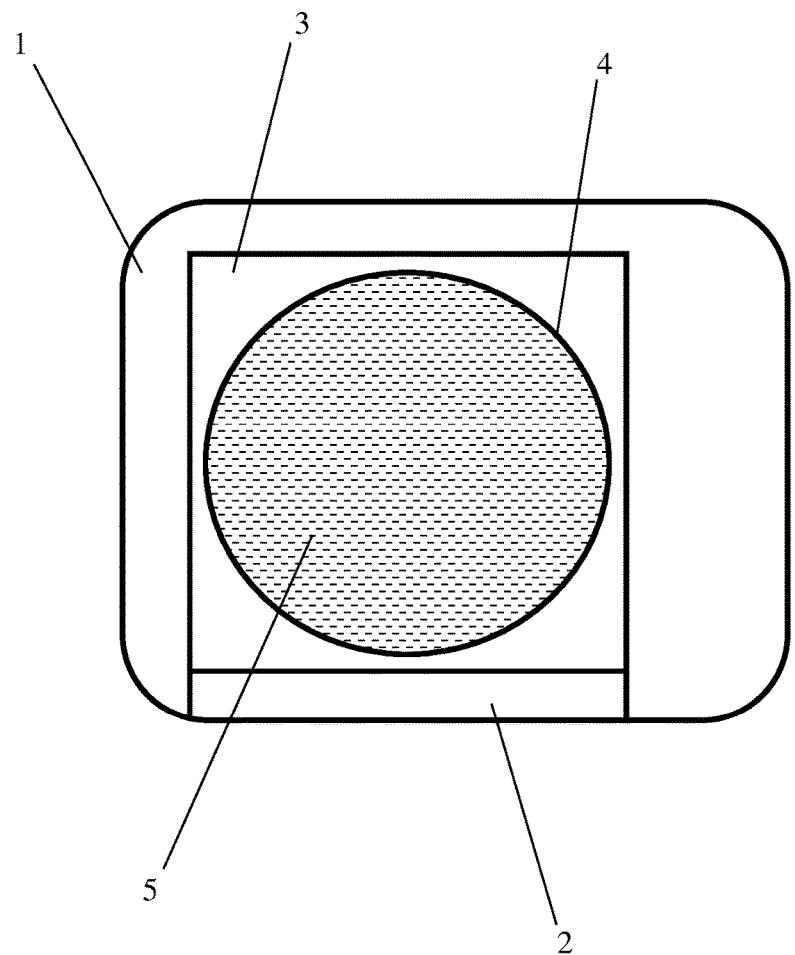
FIG. 3 is a cross-sectional view of the apparatus shown and described in connection with FIGS. 1 and 2, generally taken along the indicated A-A line shown in FIG. 1.
Figure 4:
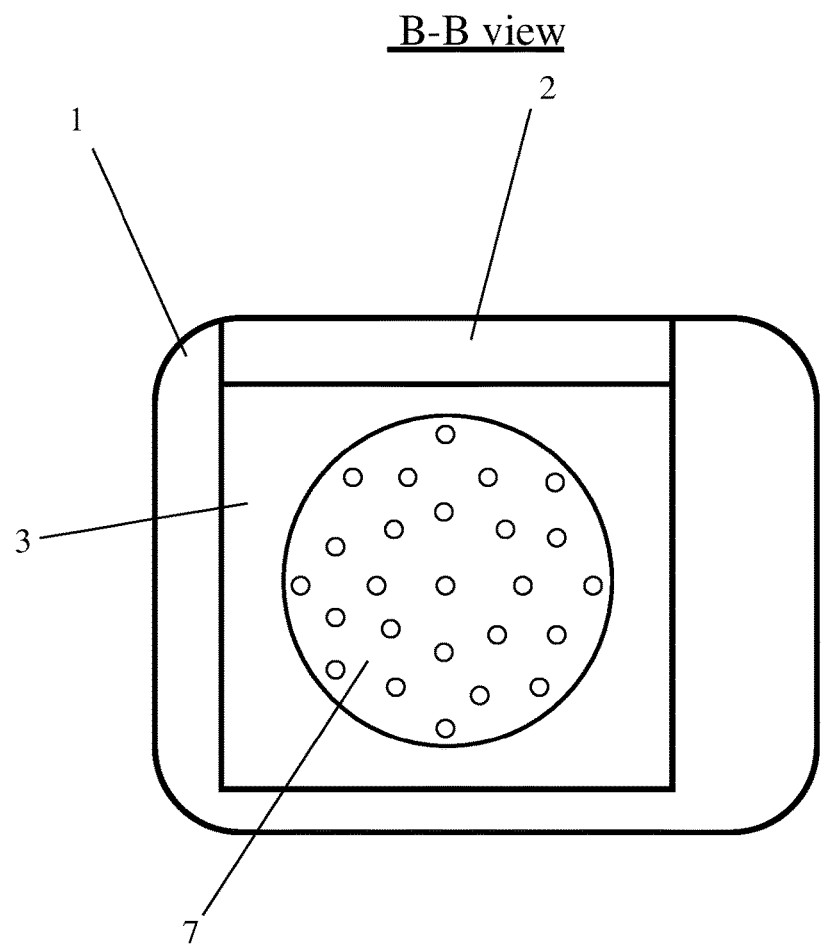
FIG. 4 is a cross-sectional view of the apparatus shown and described in connection with FIGS. 1 and 2, generally taken along the indicated B-B line shown in FIG. 1.

The device is schematically illustrated by reference to FIGS. 1-4 of the DRAWINGS, where FIG. 1 shows the exterior of an exemplary device or apparatus that practices the principles of the present invention. FIG. 2 illustrates preferred interior components to implement the techniques or methodologies of the present invention. FIGS. 3 and 4 illustrate views of the device of FIG. 1, taken along the lines A-A and B-B in the figures, respectively.

With reference now to the DRAWINGS, a device is shown that may be employed in practicing the invention, generally designated by the reference numeral 1, which includes a housing 2 with a door, ventilation holes in the sides and an inner chamber 3, as shown in FIGS. 2-4. On a lower base of the inner chamber 3 is another chamber, generally designated by the reference numeral 4, which may constitute a cuvette shape 5 and include therein an aforedescribed photoactivated liquid (such as an aqueous solution of methylene blue), generally designated by the reference numeral 6.

With further reference to the DRAWINGS, particularly to FIGS. 2 and 4 thereof, there is shown an emitter of monochromatic light, generally designated by the reference numeral 7, which is mounted to an upper base 8 of the interior of inner chamber 3. Exposure time of the emitters can be set by use of a timer knob 9, as shown in FIGS. 1 and 2, where each division of the scale thereon can correspond to 15 minutes, and the total time given by the timer in one embodiment is 90 minutes. In a preferred embodiment of the present invention, the monochromatic emitter 7 is activated by turning the aforementioned timer knob 9 in a clockwise direction with the door closed. When the set exposure time expires, the treatment is done automatically. A signal indicator light, generally designated by the reference numeral 10, preferably indicates when the device 1 is in operation.

In the case of a premature opening of the housing door 2, in a preferred embodiment the monochromatic emitter 7 is switched off.

Various ways to utilize the apparatus of the present invention are now shown.

Medical instruments are placed in the cuvette 5 within the aforementioned aqueous solution of methylene blue 6, and the aforementioned door closed. The medical devices in the chamber 4 are then subjected to irradiation by emitters 7 of light energy, such as monochromatic radiation with a maximum specific content of monochromatic light with a wavelength of 590 nm or 660 nm, with a total light output of not less than 280 lm. The exposure time may be set to 90 minutes, e.g., using the aforesaid timer 9. After treatment, in the device 1, the viruses remaining on the medical instruments are completely inactivated, i.e., the viruses lose their ability to infect cells of the human body. Instruments so sterilized are then reliably reused without risk of infecting patients.

In a preferred embodiment of the present invention, the aforementioned monochromatic light emitter 7 has a maximum specific content of a monochromatic beam with a wavelength of 590 nm or 660 nm, with a total capacity of not less luminous flux 280 lm, is made in the form of LEDs, evenly placed on the panel or upper base of the chamber 3, as shown in FIG. 4, and calibrated in the emission spectrum with a wavelength range of 582-592 nm or 658-662 nm.

Verification steps of the employment of the claimed apparatuses and methods within an installation and carried out on in a biological environment contaminated by viruses, such as blood plasma.

Example 1 Shows a First Exemplary Usage

Monochromatic radiation emitters 7 with a range of 590±2 nm are employed. After treatment in the inventive installation method, i.e., within device 1, samples of HBV containing plasma were treated for 90 minutes in a 0.01% solution of methylene blue, and afterward the amount of lymphocytes, computed by Polymerase Chain Reaction (PCR), of HBV DNA particles was zero, i.e., they were not found. This indicates that, after inactivation, the HBV completely lost the ability to penetrate the human lymphocytes.

In case of using a monochromatic radiation emitter 7 with a range of 588-592 nm, this reached full effect on HBV inactivation in a 0.01% methylene blue solution.

Example 2 Shows a Second Exemplary Usage

Monochromatic radiation emitters 7 with a range of 590±2 nm are employed. After treatment in the device 1, samples of HBV containing plasma were treated for 90 minutes in a 0.02% solution of methylene blue. As above, the amount of lymphocytes, computed by PCR, of HBV DNA particles were not found. This indicates that, after inactivation, HBV completely loses the ability to penetrate the human lymphocytes.

This also means that, when using monochromatic radiation emitters 7 with a range of 588-592 nm, the full effect of HBV inactivation in 0.02% methylene blue solution was reached.

Example 3 Shows a Third Exemplary Usage

Monochromatic radiation emitters 7 with a range of 660±2 nm were employed. After treatment in the device 1, as set forth hereinabove, samples of HBV containing plasma were treated for 90 minutes in a 0.01% solution of methylene blue. Again, the lymphocytes, computed by PCR, found no HBV DNA particles. This again indicates that, after inactivation, HBV completely lost the ability to penetrate the human lymphocytes.

In case of using monochromatic radiation emitters 7 with a range of 658-662 nm, the full sterilization treatment effect was reached by inactivating HBV inactivation in 0.01% methylene blue solution.

Example 4 Shows a Fourth Exemplary Usage

Monochromatic radiation emitters 7 with a range of 660±2 nm were employed. After treatment in the device 1, as discussed, samples of HBV containing plasma were treated for 90 minutes in a 0.02% solution of methylene blue, and no lymphocytes, computed by PCR, of the HBV DNA particles were found.

This further indicates that, after inactivation, HBV completely loses the ability to penetrate the human lymphocytes.

In case of using monochromatic radiation emitters 7 with a range of 658-662 nm, the full effect on HBV inactivation in 0.02% methylene blue solution was reached.

Thus, as shown in the various examples, the use of the principles of the claimed invention can effectively and cost-effectively achieve complete inactivation of RNA and DNA viruses on medical instruments and can be offered for wide practical use in health care facilities.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the breadth or scope of the applicant's concept. Furthermore, although the present invention has been described in connection with a number of exemplary embodiments and implementations, the present invention is not so limited but rather covers various modifications and equivalent arrangements, which fall within the purview of the appended claims.

The invention claimed is:

1. A method for inactivating RNA and DNA contained in viruses on medical instruments, comprising:
    preparing a methylene blue aqueous solution having a concentration from about 0.01% to about 0.02%,
    immersing at least one medical instrument into a container containing said methylene blue aqueous solution, said container being within a housing;
    sealing said container within said housing; and
    irradiating, by a monochromatic light source within said housing and above said container, said methylene blue aqueous solution in said container with monochromatic radiation for at least about 90 minutes,
    wherein said monochromatic light source emits a total light output of said monochromatic radiation on said methylene blue aqueous solution greater than about 280 lumens,
    whereby RNA and DNA of viruses on said at least one medical instrument are inactivated.

2. The method according to claim 1, further comprising, prior to the step of immersing, the step of:
    washing said at least one medical instrument.

3. The method according to claim 1, wherein said monochromatic light source is at least one emitter and said monochromatic radiation is within a wavelength range of about 582-592 nm.

4. The method according to claim 1, wherein said monochromatic light source is at least one emitter and said monochromatic radiation is within a wavelength range of about 658-662 nm.

5. The method according to claim 1, wherein said monochromatic light source comprises at least one LED.

6. The method according to claim 1, further comprising, after the step of irradiating, the step of:
    unsealing said housing and removing said at least one medical instrument.

7. The method according to claim 6, wherein said at least one medical instrument has been immersed in said solution for at least about 90 minutes before said unsealing.

* * * * *